(12) United States Patent
Jiang

(10) Patent No.: US 11,622,880 B2
(45) Date of Patent: Apr. 11, 2023

(54) SELF-APPLICABLE CONDOM

(71) Applicant: Youlin Jiang, Brampton (CA)

(72) Inventor: Youlin Jiang, Brampton (CA)

(*) Notice: Subject to any disclaimer, the term of this patent is extended or adjusted under 35 U.S.C. 154(b) by 258 days.

(21) Appl. No.: 17/084,138

(22) Filed: Oct. 29, 2020

(65) Prior Publication Data

US 2022/0133526 A1    May 5, 2022

(51) Int. Cl.
*A61F 6/04* (2006.01)
*A61F 6/00* (2006.01)

(52) U.S. Cl.
CPC .............. *A61F 6/04* (2013.01); *A61F 6/005* (2013.01)

(58) Field of Classification Search
CPC .................... A61F 6/005; A61F 6/04
See application file for complete search history.

(56) References Cited

U.S. PATENT DOCUMENTS

| | | | |
|---|---|---|---|
| 5,549,120 A * | 8/1996 | Persson | A61F 6/00 128/842 |
| 2010/0071702 A1* | 3/2010 | Sturlingh | A61F 6/04 128/842 |

* cited by examiner

*Primary Examiner* — Vishal V Vasisth

(57) ABSTRACT

A packaged condom applicator apparatus is provided with a condom supplied therein. The apparatus has the following: a condom holder where the base of the condom can be inserted and secured in place while protecting the condom body as packaging; an apparatus clip or unhinged clip that presses down on the condom tip to create a reservoir and an airtight seal during condom application. This helps avoid the creation of air bubbles. Using the condom holder, the user simply slides the condom along the erected penis to apply the condom on and removes the condom holder, opening the condom tip clip automatically, and ejecting the whole apparatus after the condom is applied onto the penis. Using this self-applicable apparatus, the user can quickly use the condom with less effort, distraction, and manual intervention.

14 Claims, 5 Drawing Sheets

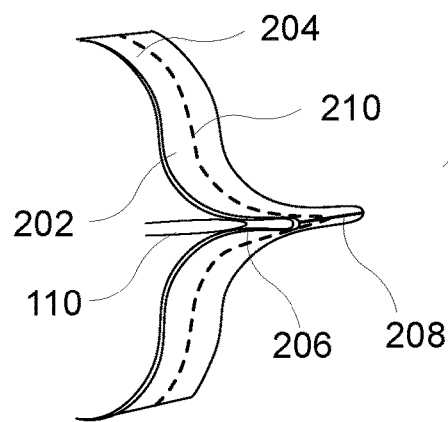
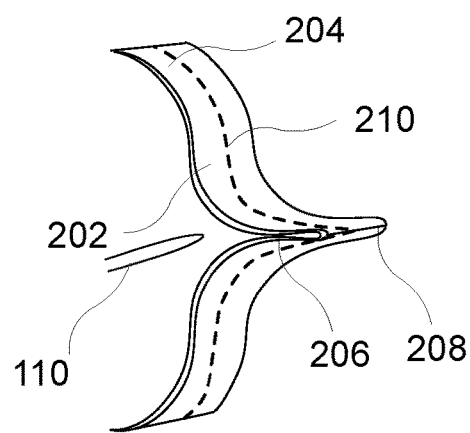
FIG. 2A  FIG. 2B
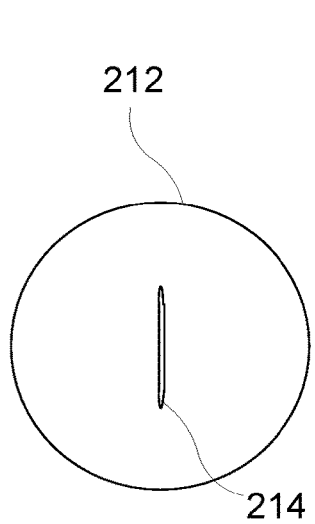
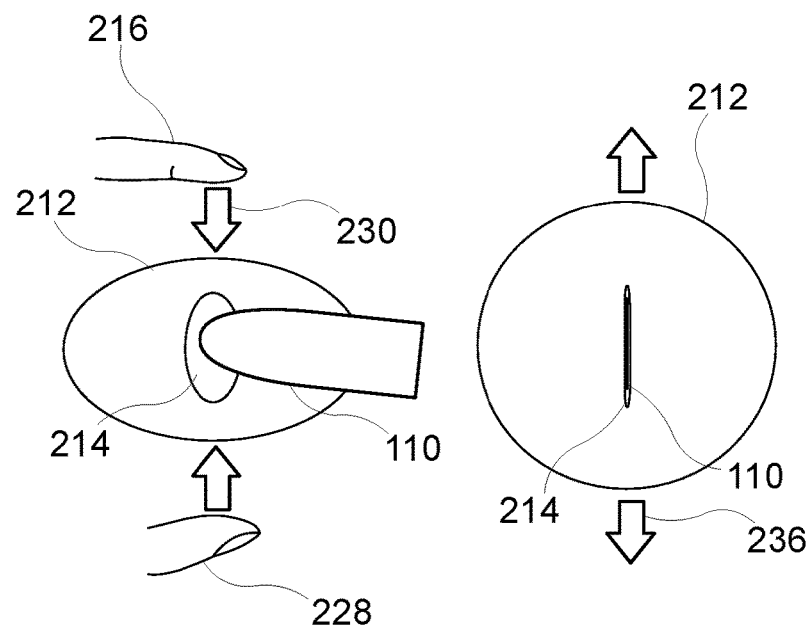
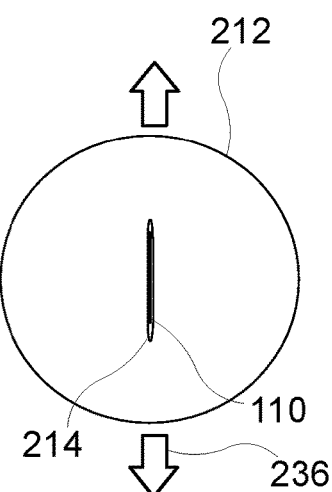
FIG. 2C  FIG. 2D  FIG. 2E

SELF-APPLICABLE CONDOM

FIELD

The present disclosure is in the field of mechanical engineering, public health, non-medical devices, contraceptives, male contraceptives, male condoms, condom holders and applicators, condom packaging, and especially, a self-applicable condom and its packaging.

BACKGROUND

Male condoms are sheath-shaped barriers made of natural latex or any other suitable material, partially or wholly covering the penis. Condoms are used during sexual intercourse to block undesirable body fluids (i.e., semen, vaginal fluids, etc.). They are effective (approximately 80-95% of the time) in protecting against sexually transmitted diseases/infections and preventing an unwanted pregnancy. Condoms are also cheap, convenient, and simple to use.

However, putting on a condom presents several challenges during sexual intercourse: (1) the environment is usually dark, so it is difficult to handle and operate; (2) improper application may damage the condom. This is mainly due to excessive manual handling; (3) air can be left in the condom tip; (4) it can take a long time and much effort to unpack and put on the condom. This may ruin an intimate moment and lead to a reduction or fading of lust and excitement during sexual intimacy, which could eventually lead to a flaccid penis (loss of erection).

Condoms can only be applied in one direction. A condom applied in the wrong direction has to be thrown away, and the user needs to apply a new condom onto the penis. Steps in applying a condom include opening the package, pinching the tip, putting the condom on, sliding the condom along the penis, and unrolling. So, a man attempts to put a condom on during an intimate moment with a partner; it can be difficult to determine the correct side for placing and unrolling the condom onto the penis in the dark. Thus, there is a risk of applying it in the wrong direction.

The condom may break, damage, tear, or rupture due to excessive handling or misuse. This commonly happens due to exposure to fingernails or jewelry. It can also happen when the condom is forcefully applied, especially in the wrong direction. In addition, condoms may break due to other reasons, such as a lack of lubricant or the presence of air bubbles.

Pinching the condom's tip is a critical step of the condom application: first, the tip creates a reservoir, air sac, or space for storing semen during ejaculation. Without this reservoir, semen collected at the tip may cause the condom to break or slide off the penis, which may cause an unexpected pregnancy; second, it pushes air away from the condom tip, forming a vacuum in the tip to store the semen. Failure to pinch the tip may create air bubbles in the condom, which may lead to condom breakage and semen spilling, which defeats the purpose of using a condom. Therefore, it would be desirable to overcome the above-discussed limitations and provide a better solution for using a condom.

The present disclosure solves the above-mentioned problems by providing a self-applicable condom design, which eliminates the difficult steps mentioned above by applying the condom in a simple and easy step by the user. The design improves upon existing condoms and their packing designs by: (1) improving the overall experience for the condom user; (2) making the condom easier to put on; (3) shortening the total time of condom application; (4) reducing the chance of condom breakage; (5) preventing incorrect application and usage; (6) providing an airtight sealed tip; and (7) still being cost-efficient and portable.

SUMMARY

The present disclosure provides a novel apparatus for a self-applicable condom that improves condom usage experience by automatically completing all the steps of applying a condom onto the penis without much of the user's attention and operation. The apparatus takes the form of a short, fat, and hollowed cylindrical prism, which comprises the condom and applicator in an all-in-one package. The apparatus contains: two seal covers at the top and bottom openings/ends of the apparatus; a condom holder and dispenser ring where the base ring of the condom can be inserted and locked; a condom wrap that covers the condom body; lubricant inside the self-applicable condom between the condom and the wrap. In a preferred embodiment of the present disclosure, the apparatus also contains a hinged tip clip for creating a vacuum seal at the condom tip to form a reservoir and keep air out during application.

Using the preferred embodiment of the present disclosure, the user can apply a condom onto the penis with the apparatus using the following steps: (1) unseal the lids of the apparatus; (2) rotate the hinged tip clip to point outwards; (3) slightly expand the wrap outwards; (4) insert the penis into the condom through the rear base opening. During this time, the holder, wrap, and hinged tip clip will touch the glans and the corona of the penis to provide stimulus to keep it erected for easy application while providing a better sexual experience; (5) slide the condom holder along the erect penis. As the condom is being put on, the wrap will also be fully expanded out. At the same time, the lubricant will be applied to the condom. This lubricant prevents condom rupture due to friction from the condom wrap or from condom use. In one variation of the preferred embodiment, the penis applies force to the hinged tip clip during condom insertion, causing the hinged tip clip to open up and fall off; (6) slide the condom holder outwards from the penis root to the tip to eject the apparatus. In another variation of the preferred embodiment, the hinged tip clip will be forced open and ejected when it comes in contact with the condom holder. The condom is fitted snugly onto the penis as the whole apparatus is ejected; (7) remove the condom from the penis as it is normally removed after use.

In an alternative embodiment of the present disclosure, the hinged tip clip is not present to pinch and secure the condom tip in place. Instead, an unhinged pinching tip clip pinches the condom tip with its inner walls that define the vertical opening or slit. Hereinafter, the term vertical opening in the context of the unhinged pinching tip clip is interchangeable with unhinged tip clip opening or slit. The top and bottom edges of the unhinged pinching tip clip can be squeezed to expand the vertical opening to allow the insertion of the condom tip. The unhinged pinching tip clip is connected to the condom holder through a snap-fit mechanism.

Using the alternative embodiment, the user applies a condom holder onto the penis in a similar manner as the preferred embodiment. However, no rotation of the condom tip is required, as it is facing forward when held by the unhinged pinching tip clip. When the condom holder slides along the penis, the unhinged pinching tip clip dislodges from the condom tip. In one variant of the alternative embodiment, the unhinged pinching tip clip wholly detaches from the apparatus. In another variant, the unhinged pinching tip clip slightly drops with the condom tip and gets dragged back by the condom holder's movement and the penis' positioning. The condom is applied, and the condom holder is ejected from the apparatus. The unhinged pinching tip clip is then ejected as it comes in contact with the condom holder.

By using this apparatus, the overall experience of using a condom can be improved. It allows the user to easily and quickly slide the condom onto the penis. It also reduces condom breakage due to less manual handling of the condom. The apparatus is also designed to prevent improper application and usage of the condom. A hinged or unhinged clip compresses the condom's tip to seal air out as the user puts on the condom. In addition to all these advantages, the condom can still maintain a small and convenient carrying size while having a low cost.

BRIEF DESCRIPTION OF THE DRAWINGS

The accompanying drawings, which are included to provide a further understanding of the invention and are incorporated in and constitute a part of this application, illustrate embodiment (s) of the present disclosure and, together with the description, serve to explain the principle of the invention. For simplicity and clarity, the figures of the present disclosure illustrate a general manner of construction of various embodiments. Descriptions and details of well-known features and techniques may be omitted to avoid unnecessarily obscuring the discussion of described embodiments of the present disclosure. It should be understood that the elements of the figures are not necessarily drawn to scale and that the dimensions of some elements may be exaggerated relative to other elements for enhancing the understanding of described embodiments. In the drawings:

FIGS. 2A-2B are the side cross-section views of the self-applicable condom's hinged tip clip holding the condom tip in the preferred embodiment;

FIGS. 2C-2E are the rear views of the unhinged pinching tip clip in the alternative embodiment of the present disclosure;

DETAILED DESCRIPTION

Figure 1:
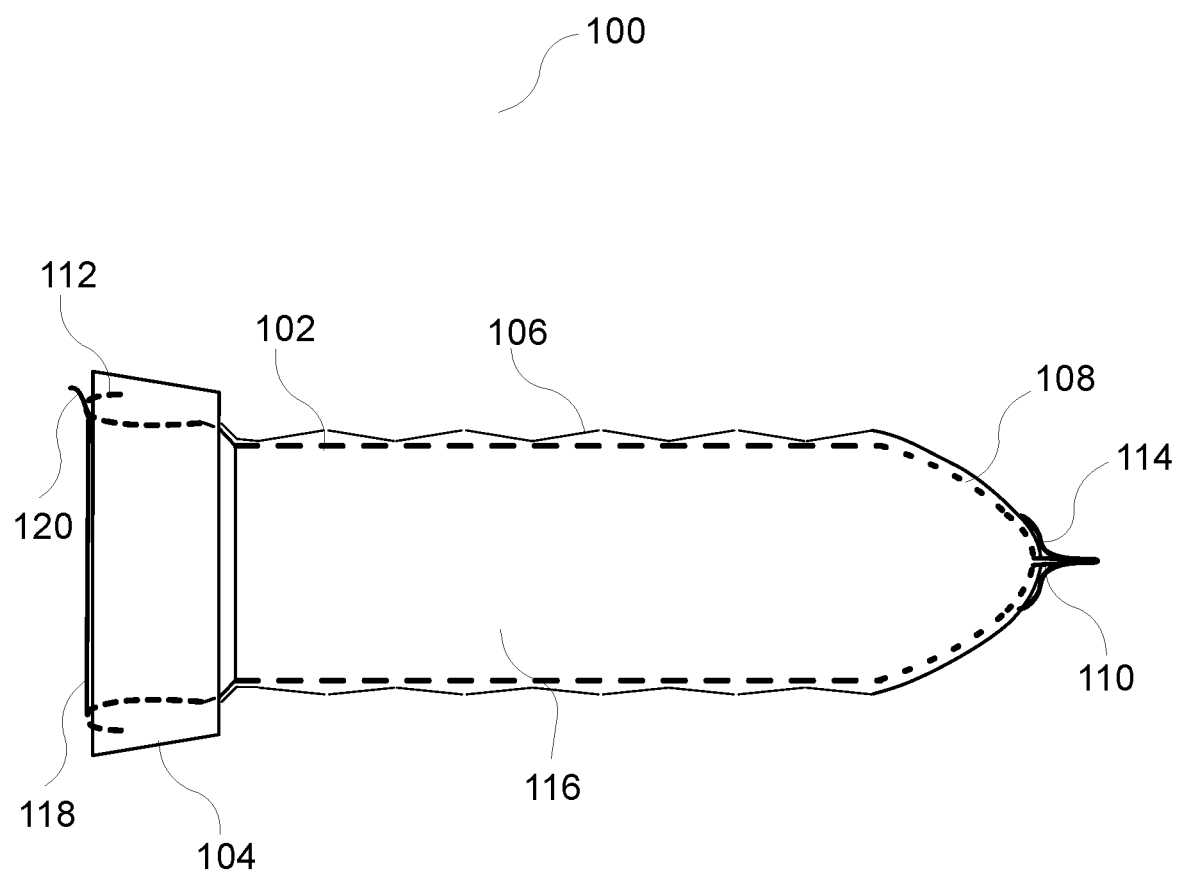
FIG. 1 is the side view of the self-applicable condom of a preferred embodiment of the present disclosure.

The present disclosure generally relates to a self-applicable condom that may take a variety of forms. Various examples of the present invention are shown in the Figures. However, the present invention is not limited to the illustrated embodiments. Reference will now be made in detail to some embodiments of the present invention, examples of which are illustrated in the accompanying figures.

The language employed herein only describes particular embodiments; however, it is not intended to be limited to the specific embodiments of the disclosure. Within the disclosure, the term "and/or" includes any and all combinations of one or more associated items. Unless indicated, "a", "an", and "the" can encompass both the singular and plural forms within the disclosure. It should also be noted that "they", "he/she", or "he or she" are used interchangeably because "they", "them", or "their" are now considered singular gender-neutral pronouns. The terms "comprises" and/or "comprising" in this specification should specify the presence of stated features, steps, operations, elements, and/or components; however, they do not exclude the presence or addition of other features, steps, operations, elements, components, and/or groups. Unless otherwise defined, all terminology used herein, including technical and scientific terms, have the same definition as what is commonly understood by one ordinarily skilled in the art, typically to whom this disclosure belongs. It will be further understood that terms, such as those defined in commonly used dictionaries, should be interpreted as having the same meaning as defined in the context of the relevant art and the present disclosure; such terms will not be construed in a romanticized or overly strict sense unless explicitly described herein. It should be understood that multiple techniques and steps are disclosed in the description, each with their own individual benefit. Each technique or step can also be utilized in conjunction with a single, multiple, or all of the other disclosed techniques or steps. For clarity, the description will avoid repeating each possible combination of the steps unnecessarily. Nonetheless, it should be understood that such combinations are within the scope of the disclosure and the claims.

In the following description, specific details are mentioned to give a complete understanding of the present disclosure. However, it may likely be evident to one ordinarily skilled in the art; hence, the present disclosure may be applied without the mention of these specific details. The present disclosure is represented as few embodiments; however, the disclosure is not necessarily limited to the specific embodiments illustrated by the figures or description below. The description of the present disclosure will now be interpreted by specifying the appended figures representing preferred or alternative embodiments.

The present disclosure provides a new apparatus and designs for a self-applicable condom that improves the condom application process for the user by simplifying the process for the user to quickly and efficiently put on a condom. Hereinafter, the term user explicitly implies a male user. The self-applicable condom is used to apply a condom onto the penis prior to sexual intercourse without the need to excessively handle the condom. The apparatus comprises a short, hollow cylindrical prism in the form of a condom applicator ring with an attached condom, stored at the hollow center within the inner walls of the condom applicator. Hereinafter, the term apparatus is interchangeable with a self-applicable condom. The term applicator is interchangeable with holder and dispenser. In one preferred embodiment, the hollow cylindrical prism has two round openings. They are the top and bottom openings, also called the front and base openings. They may have different sizes: a larger opening of the condom holder at the base of the apparatus for the user to insert the penis into the condom's opening space during condom application; a slightly smaller opening at the front of the apparatus, where the condom tip is located. Hereinafter, the larger opening at the rear base of the condom is referred to as the base or rear opening. The smaller opening at the front near the condom's tip is referred to as the front or tip opening. Each opening is covered by a seal cover that is removable via a latch tab.

The self-applicable condom also contains a component that secures the condom tip in place to create a reservoir and an airtight seal during condom application. A number of embodiments of the present disclosure relate to the component creating the reservoir and the airtight seal at the condom tip, as well as the means to eject that component during condom application. In the preferred embodiment of the present disclosure, the self-applicable condom also contains a flexible hinged tip clip at the front end of the entire apparatus that holds the condom tip in place. In doing so, the condom tip creates a reservoir, and the hinged tip clip keeps air out as the condom is applied onto the penis via the condom holder. Hereinafter, the term tip clip is interchangeable with clip, apparatus clip, and hinged clip. The term hold in the context of the tip clip is interchangeable with bind, clamp, press, and secure. This hinged tip clip may be made of a resilient material. That is, a portion of the clip may remember and keep its current position unless a force above a threshold is applied to it. The hinged clip consists of multiple portions working together that allow the clip to open up during the apparatus' ejection: a handle portion located at the top and bottom edges of the hinged clip; an attached portion connected to the condom wrap; and a clamping portion that holds down on the condom tip. The hinged clip can be removed in two ways: (1) the penis pushes against the hinged tip clip as the condom holder applies the condom onto the penis. Because of the hinged clip's lightweight, the force exerted is enough to open the hinged clip tip portions; (2) the condom holder moves forward after the condom is put on, which pushes against the hinged clip. This causes the hinged tip clip to open up by itself and detach from the condom tip as the entire apparatus is ejected. The hinged tip clip does not damage the condom and the wrap according to the present disclosure. Hereinafter, the term eject is interchangeable with release, remove, dislodge, and displace.

In an alternative embodiment, the condom tip is secured in place by an unhinged pinching tip clip. Hereinafter, the term unhinged pinching tip clip is interchangeable with unhinged tip clip or unhinged clip. The unhinged pinching tip clip securely holds the condom tip using a vertical opening comprising the cap's inner walls. This opening can widen horizontally by pressing the unhinged clip's top and bottom edges, aligning with the endpoints of the vertical opening. When the condom tip is inside this vertical opening, the pressure used to open the vertical opening can be released to secure the condom tip within the walls of the vertical opening. The unhinged pinching tip clip is also snap-fitted to the condom holder at the time of assembly; this can be detached when the user inserts the penis through the base opening. Once detached, the unhinged clip can be removed in two ways: (1) the unhinged clip falls off entirely after detaching from the condom holder. This is due to its weight; (2) the unhinged clip and the secured condom tip slightly drop and hang. They are then dragged back and moved along the penis by the condom holder. Once the condom is completely on, the holder moves forward towards the tip to eject the entire apparatus and the pinching tip clip with it. This causes the unhinged tip clip to detach from the condom tip as the entire apparatus is ejected. The unhinged tip clip does not damage the condom and the wrap according to the present disclosure. Hereinafter, both hinged and unhinged tip clip may be all called tip clips.

A condom wrap is integrated as part of the self-applicable condom apparatus. The condom wrap covers the condom and is also compressed within the inner walls of the condom holder. As the condom holder slides along the penis shaft, the condom wrap decompresses and extends along the penis following the condom holder's movement. At the same time, the condom wrap applies lubricant along the length of the condom as the condom holder slides inwards towards the penis root along the penis shaft. When the condom is applied and the holder moves forward, the condom wrap compresses; it is then ejected along with the rest of the apparatus.

With the new apparatus and embodiment designs, the self-applicable condom addresses problems previously found in existing condoms. First, the apparatus is designed in a way that allows users to easily identify which side to apply the condom on, even in the dark. This is achieved with the smaller opening at the front, indicating the condom's tip, and the larger opening at the rear base, indicating the side that the user applies the condom. In a sense, the user can feel and determine the correct side to apply the self-applicable condom without the need to see it. Furthermore, the apparatus can be applied with one hand and in relatively fewer motions, making it easier and quicker to apply a condom onto the penis.

Second, the apparatus also prevents improper application and reduces the risk of damaging the condom. One way it does this is by preventing excessive manual handling of the condom, which prevents the condom from being torn by fingernails or jewelry. The user primarily holds the condom holder rather than the condom itself during application. Also, the self-applicable condom is designed in a way that prevents improper application, mainly through the shape of the condom holder, as noted earlier. Because of how the design visually demonstrates the correct side of insertion, the user is less likely to force the condom on the wrong way.

Furthermore, both the hinged tip clip in the preferred embodiment and the unhinged pinching tip clip in the alternative embodiment pinch down on the condom tip. Their presence further removes the need to manually handle the condom during its application, particularly when pinching the tip. The clip creates an airtight vacuum seal at the condom tip, which forms the reservoir for catching semen. It also prevents air from entering the condom body and creating air bubbles. The lack of air in the condom's opening space also prevents semen from escaping to the root of the penis. Because of this, there is a reduced risk of the condom breaking and failing due to improper application or misuse.

Condom damage is further prevented in additional ways. The self-applicable condom also reduces the risk of damage to the condom through the packaging design of the condom itself. The condom is attached to a condom holder via its base ring. The tip clip mentioned before is rotated to its side to fit inside the condom holder. Both the condom holder's top and bottom openings are covered by seal covers, which can be removed via attached latch tabs. In addition to protecting the condom, the entire apparatus is still compact enough to maintain its portability.

The alternative embodiment for the self-applicable condom of the present disclosure also achieves additional protection for the condom while maintaining portability. Unlike the preferred embodiment, there is no seal cover at the front opening or any need to rotate a hinged tip clip at the front. Rather, the unhinged pinching tip clip securely holds the condom tip outwards. The unhinged pinching tip clip also acts as a protective cover for the front opening of the apparatus; it can also fit onto the condom holder via a snap-on mechanism. The design of the apparatus in the alternative embodiment is still considered a small and compact structure for portability.

Some embodiments have a lubricant between the condom and condom wrap. In other embodiments, the condom may be pre-lubricated and would not need additional lubrication. Both the condom and the condom wrap are compressed inside the inner walls of the condom holder. Because of the condom wrap (e.g., foil) and its proximity to the condom itself, the wrap may rub against the condom as it is compressed inside the condom holder. This friction may cause the condom to tear. The condom may also tear from friction during sexual intercourse if not properly lubricated. Therefore, the addition of lubricant during the condom application via the apparatus helps reduce the risk of such damage.

Third, the apparatus reduces the time needed to put on a condom by simplifying the process. In the preferred embodiment, the process starts with the seal covers being removed with the attached latch tabs. The user then places and rolls the condom holder along the penis, which applies the condom on. Once the condom is fully on the penis, the user rolls the holder outwards to eject the apparatus. Additionally, the tip clip holds down on the tip of the condom to create a reservoir, which also saves the user time. This tip clip also ejects automatically through the force exerted by the penis during condom application or by the holder's ejection. This simplified and quickened process of applying a condom means that there is less distraction during intimacy.

The alternative embodiment follows a similar process as the preferred embodiment with a few differences: first, only one seal cover needs to be removed at the base of the apparatus; second, the condom tip does not need to be adjusted since it is already facing outwards thanks to the way the unhinged pinching tip clip holds it; third, when the penis is inserted through the condom holder's base opening, the unhinged pinching tip clip automatically detaches from the sliding movement of the condom holder to the root of the penis. In another word, the pushing force exerted by the penis (specifically the glans) during insertion aids the detachment of the unhinged clip. Once detached, the unhinged pinching tip clip falls off automatically, or it can be dragged back during condom application and then removed by the condom holder's ejection.

The self-applicable condom also adds to the intimacy of sexual intercourse by providing stimulus to the penis during condom application. Due to the tip clip, the lack of air during condom application allows the condom's distal end to tightly wrap around the glans at the tip of the penis and the corona at the base of the glans. These areas of the penis (glans and corona) are highly sensitive, which will keep the user stimulated and the penis erect. Another way this is achieved is through the sliding motion of the condom holder itself. The inner diameter condom holder slides along an erect penis as it unrolls the condom. This movement keeps the penis stimulated for a brief moment, long enough for the user to commence sexual intercourse.

FIG. 1 is a side view of the self-applicable condom apparatus of a preferred embodiment of the present disclosure. The apparatus (100) comprises a condom holder (104) in the shape of a hollow, thick, cylindrical prism or ring structure. The base opening at the rear base of the condom holder (104) is sealed by a seal cover (118) that is removed by a latch tab (120) integrated with the seal cover (118). Hereinafter, the seal cover and latch tab are referred to as the base seal cover (118) and base latch tab (120).

Attached to the base of the condom holder (104) is a condom consisting of the following sections: an external condom body (102); a hollow opening space (116) inside the condom body (102), where the penis is inserted to put on the condom; a distal end (108) that is part of the external condom body (102) covering the glans and corona at the front of the penis; a condom tip (110) in front of the distal end (108) is located at the forefront of the condom. The condom tip (110) forms the reservoir for catching semen; a condom base ring (112) at the rear of the condom that attaches to the rear side of the condom holder (104). The condom base ring (112) also holds a portion of the condom body (102) that is rolled up, which unrolls as the condom is applied onto the penis. Hereinafter, the term condom generally refers to its collective sections that include the condom body (102), the distal end (108), the condom tip (110), and the condom base ring (112). The condom (102, 108, 110, 112) is compressed in a rolled-up fashion within the inner walls of the condom holder (104), which stretches and extends along the penis from the glans pointing outwards to the root near the body. Most of the condom body (102) is covered by a condom wrap (106), including the distal end (108) and the condom tip (110) at the front of the condom (102, 108, 110, 112). A hinged tip clip (114) is attached to the condom wrap (106) at the apparatus' (100) front. This hinged clip (114) holds the condom tip (110) to form a reservoir and an airtight seal during application.

The condom holder (104) is made of a stable plastic, which can be injection molded at the time of manufacturing. Plastic is considered one of the several suitable materials because it is rigid enough to maintain its shape. Additionally, the plastic material is lightweight and cheaper to manufacture. This allows the self-applicable condom (100) apparatus to maintain its portability and cost-efficiency. In other embodiments, the condom holder (104) can be made of other materials, including rubber, latex, etc. Such materials may be more durable but are also heavier. Thus, the apparatus' (100) portability would be affected.

In yet another embodiment, the condom holder (104) can include a handle to further ease the handling of the apparatus (100) during condom application; however, the handle may affect the compact and portable design of the self-applicable condom (100).

The condom wrap (106) serves as a means of protection for most of the condom body (102), including the distal end (108) and condom tip (110), collectively termed wrapped areas of the condom for explanation purposes. This wrap (106) can be made of plastic, foil, or any other suitable material. Due to its close contact with the wrapped areas of the condom (102, 108, 110), there is a possibility that direct contact may rub against the wrapped areas of the condom (102, 108, 110) to cause a rupture. This is mitigated in the present disclosure by adding lubricant between the condom wrap (106) and the wrapped areas of the condom (102, 108, 110). The lubricant is distributed throughout the wrapped areas of the condom (102, 108, 110) as the apparatus slides the entire condom (102, 108, 110, 112) onto the penis; this will be demonstrated and explained in FIGS. 4A-4C.

The condom wrap (106) in the present disclosure is integrated with the self-applicable condom (100) as a non-removable component. It is permanently bonded to the condom holder (104); the condom wrap (106) can be glued, taped, stapled, etc. In one way, this allows the apparatus (100) to be disposed of as one neat package after the condom (102, 108, 110, 112) is applied onto the penis and the condom holder (104) is brought forward to the tip to dispose of the entire apparatus (100); this will be mentioned in FIGS. 5A-5B. In another embodiment, the condom wrap (106) is removable and disposed of separately. In yet another embodiment, the condom wrap (106) is not included as part of the apparatus (100). The condom (102, 108, 110, 112) is then exposed to the inner walls of the condom holder (104); this may cause the condom (102, 108, 110, 112) to break due to friction, particularly if there is no lubricant to facilitate the movement of the condom holder (104) from the tip of the penis to the base or root.

The condom (102, 108, 110, 112) presented in the present disclosure is shown as one type and size. In another embodiment, the apparatus (100) can support different condom (102, 108, 110, 112) styles, such as a ribbed condom (102, 108, 110, 112). Another embodiment of the apparatus (100) can support different condom (102, 108, 110, 112) sizes; this will be explained further in FIGS. 4A-4C.

FIGS. 2A-2B are the side cross-section views of the self-applicable condom's hinged tip clip holding the condom tip in the preferred embodiment. FIGS. 2C-2E are the rear views of the unhinged pinching tip clip securing the condom tip in the alternative embodiment of the present disclosure. FIG. 2A is the side cross-section view of the hinged tip clip (114) of the preferred embodiment holding the condom tip (110) in place. The hinged clip (114) is split into multiple portions: (1) a handle portion (204), shown as the outermost sections at the top and bottom edges of the hinged clip (114) in the sub-figure. The handle portion (204) is a freely moving portion that moves away from the distal end of the condom when it is released to eject the condom tip (110), as shown in FIG. 2B; (2) an attached portion (202) is attached and secured to the condom wrap with a top and bottom section at the front of the apparatus. The attached portion (202) can be glued or taped; (3) a clamping portion (206) is an elongated U-shaped portion that extends outwards along the center of the hinged tip clip (114). The clamping portion (206) holds the top and bottom of the condom tip (110) in place. Like the handle portion (204), the clamping portion (206) is also freely moving, but only enough to clamp together when releasing the condom tip (110); as shown in FIG. 2B; (4) a clip hinge (208) is located in front of the clamping portion (206). The clip hinge (208) connects the clip portions (202, 204, 206) together; (5) a wire (210) embedded within the hinged tip clip (114), which shapes the clip portions (202, 204, 206) around the glans of the penis.

The hinged tip clip (114) in the present disclosure is shown in a vertical orientation lining up with the sagittal plane, where the handle portion (204) align with the top and bottom of the condom tip (110). In another embodiment, the hinged tip clip (114) can be designed to hold the condom tip (110) in a horizontal orientation along a transverse plane. In a sense, it holds the left and right side of the condom tip (110). However, this may affect the packaging of the apparatus; this will be explained further in FIGS. 3A-3C.

FIG. 2B is the side cross-section view of the hinged tip clip releasing the condom tip (110) during condom application. The handle portion (204) at the top and bottom of the hinged tip clip (114) moves outward as the hinged tip clip (114) is ejected on its own or when the entire apparatus is ejected. The attached portion (202) is typically attached to the condom wrap. However, it can also separate from the condom wrap with the rest of the hinged clip (114) due to its light mass; this will be explained below. When the condom tip (110) is released from the hinged clip (114), the resilient top and bottom sections of the clamping portion (206) spring back together and close the gap filled by the condom tip (110). Thus, the gap between the resilient top and bottom sections of the clamping portion (206) remains minimal unless acted upon by an external force.

The hinged tip clip (114) is a key novelty of the self-applicable condom apparatus. Because the hinged tip clip (114) is already pressing down the condom tip (110) at the time of use, the user does not have to invest time and effort to pinch the condom tip (114). Therefore, it eases and quickens the condom application process while keeping the condom airtight. Furthermore, the hinged clip (114) only applies minimal pressure to the condom tip (110). Because of the tip and hinged clip's (114) ability to create the reservoir and seal out air, the condom is less likely to break from use. The airtight application also provides stimulation to the glans and corona; this will be explained later in FIGS. 4A-4C.

The condom tip (110) is meant to come out as the handle portion (204) of the hinged clip (114) opens up during the ejection of the condom holder. In one variant of the preferred embodiment, the hinged tip clip (114) can be ejected from the apparatus through the force exerted by the penis (specifically the glans) during condom application. In another variant of the preferred embodiment, the hinged tip clip (114) stays on the condom wrap during condom application and is ejected with the rest of the apparatus when in contact with the condom holder; this will be demonstrated in FIGS. 5A-5B. In case the hinged tip clip (114) is attached too tightly and cannot be released naturally by the above means, the user can move the handle portion (204) outwards to release the condom tip (110). This is mainly a supplementary action, not normally done in the condom application process using the self-applicable condom. In one way, this still helps minimize the amount of handling needed for the condom, as the user only touches that handle portion (204) rather than the condom itself.

In another embodiment, the user can manually press the handle (204) and clamping (206) portions of the hinged clip (114) to lightly pinch the condom tip (110). However, this is considered an extra step in the condom application process. In yet another embodiment, the apparatus can include an automatic mechanism to open up the hinged clip (114) in case the condom tip (110) is still held in place at the time of the apparatus' ejection.

The embedded wire (210) is just one example of how to form the hinged clip (114) to fit resiliently around the glans of the penis and the condom's distal end. A bendable metal like aluminum is preferable because of its flexibility. In another embodiment, the hinged clip (114) is a bendable plastic that can achieve the same result as a metal wire (210). In yet another embodiment, no embedded wire (210) is present within the hinged tip clip (114); however, the portions (202, 204, 206) of the hinged clip (114) may be less flexible in how it moves.

FIG. 2C is a rear view of the unhinged pinching tip clip in the alternative embodiment of the present disclosure. FIG. 2C is considered to be the rear view because the unhinged clip (212) is facing the user in the same manner as the base opening of the self-applicable condom. The unhinged pinching tip clip (212) is a plastic or silicone unhinged clip (212) that is mainly solid throughout. It contains a small vertical gap in the middle, also known as a tip insertion opening (214), which widens the inner walls of the unhinged clip (212) horizontally; this will be shown in the next sub-figure.

FIG. 2D illustrates a rear view of the unhinged pinching tip clip in the alternative embodiment of the present disclosure in an open state as the user inwardly presses the edges of the unhinged pinching tip clip (212) near the opposing ends of the small vertical gap. The user pinches the top edge of the unhinged clip (212) downwards in an inward direction (230) with their forefinger (216); the forefinger (216) can be an index, middle, ring, or pinky finger. At the same time, the user pinches the bottom edge of the unhinged clip (212) upwards in an inward direction (230) with their thumb (228) or other suitable means (e.g., other fingers or a hard surface). When both actions are done simultaneously, the tip insertion opening (214) widens horizontally to allow the insertion of the condom tip (110) into the unhinged clip (212). The inner walls of the unhinged clip (212) can hold the left and right sides of the condom tip (110).

The unhinged clip (212) in the present disclosure is shown to be pinched down from the top and bottom edges. The pressure applied in an inward direction (230) is in the same orientation as the unhinged clip opening (214) itself, as indicated by the ending points of the unhinged clip opening (214). When the unhinged clip (212) is pressed in this manner, the height of the unhinged clip opening (214) is shortened while the width expands. In another embodiment, the unhinged pinching tip clip (212) can be pressed inwards (230) from the left and right edges of the unhinged clip (212). This is achievable by merely rotating the placement of the unhinged clip (212) so that the unhinged clip opening (214) is horizontal. In a non-limiting example, the unhinged clip opening (214) would be disposed at about a 90° orientation with respect to the orientation shown in FIG. 2C. The unhinged clip opening (214) would shrink in width but expand in height. When the condom tip (110) is inserted, the inner walls of the unhinged clip (212) would close and secure the top and bottom of the condom tip (110). In other multiple embodiments, the unhinged clip opening (214) can be diagonal to any degree (e.g., on a 45° angle) as long as the forefinger (226) and thumb (228) can align at the ends of the unhinged clip opening (214).

In yet another alternative embodiment, the unhinged clip (212) can consist of multiple parts to allow the exterior to open up and expose the unhinged clip opening (214). The condom tip (110) can be placed inside, which are then sealed by bringing the unhinged clip (212) exterior together.

FIG. 2E illustrates a rear view of the unhinged pinching tip clip in the alternative embodiment of the present disclosure in a closed state after the condom tip is inserted. The unhinged pinching tip clip (212) returns to its original closed state, as shown in FIG. 2C. The condom tip (110) is now inserted into the unhinged clip opening (214), which is compressed laterally to decrease its width along the horizontal transverse plane. Meanwhile, the condom tip's (110) height dimensions along the vertical sagittal plane have increased. At the same time, the unhinged clip opening (214) also returns to its original size. As the unhinged clip (212) and unhinged clip opening (214) returns to its original size, the pressure is released in an outward direction (236) at the top and bottom of the unhinged clip (212).

Figure 3A:
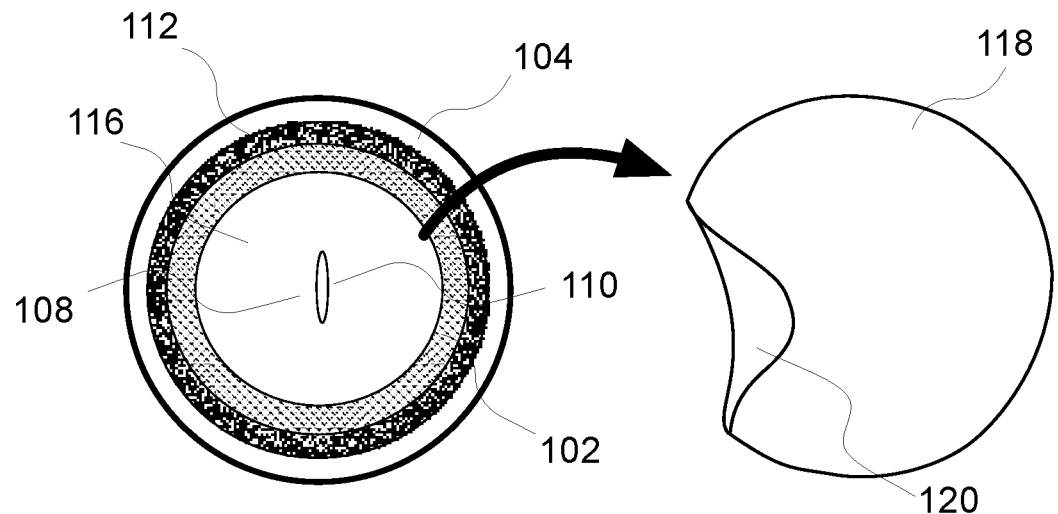
FIG. 3A is the rear view of the self-applicable condom with the base seal cover.
Figures 3B, 3C:
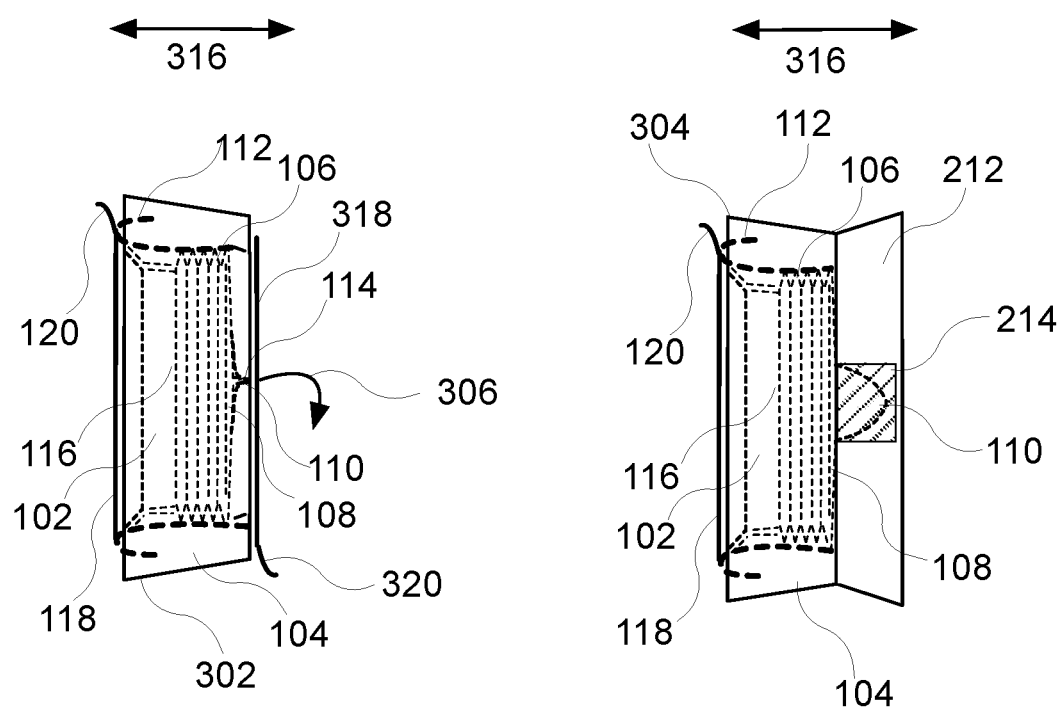
FIGS. 3B-3C are the side views of the sealed state for the self-applicable condom in both preferred and alternative embodiments of the present disclosure.

FIG. 3A illustrates a rear view of the self-applicable condom with the base seal cover. FIGS. 3B-3C are the side views of the sealed state for the self-applicable condom in both preferred and alternative embodiments of the present disclosure. FIG. 3A illustrates a rear view of the self-applicable condom facing the base opening. The self-applicable condom is positioned in an upright vertical orientation in this sub-figure. FIG. 3A also illustrates a base seal cover (118) that covers the apparatus' base opening. All descriptions of the self-applicable condom apparatus in FIG. 1 also apply here. The condom base ring (112) is attached to the condom holder (104). As it is attached, the condom base ring (112) and a portion of the condom body (102) is stretched outwards in a radial direction. The condom tip (110) and the remaining portion of the condom body (102), outlined by the condom's opening space (116) and the distal end (108), extend all the way to the other side of the condom holder (104). As shown in FIGS. 3B-3C, the base seal cover (118) lines up with the outer edge of the base opening of the condom holder (104) to protect the contents of the entire apparatus (i.e., condom (102, 108, 110, 112)). The base seal cover (118) has an attached base latch tab (120) that folds out for the user to hold in order to remove the base seal cover (118) for apparatus use.

The condom's (102, 108, 110, 112) attachment to the condom holder (104) slightly stretches a portion of the condom body (102) outwards in a radial direction. However, this does not significantly affect the tensile strength of the condom (102, 108, 110, 112) itself, especially if the condom (102, 108, 110, 112) is made of latex. The condom (102, 108, 110, 112) may be made of other suitable materials, such as plastic, polyurethane, polyisoprene, lamb's intestine, nitrile, silicone, etc. The condom base ring (112) can be attached to grooves or holding formations (e.g., hooks) within the annular area of the condom holder (104).

In another embodiment, the condom holder (104) can contain multiple parts (e.g., rings). For example, an outer auxiliary ring with a greater axial width can cover the condom holder (104) in the present disclosure. The outer auxiliary ring could attach to the condom holder (104) through a snapping mechanism. This outer ring enables the condom holder's (104) inner diameter to be small enough so that it does not stretch the condom base ring (112) and the affected portion of the condom body (102).

FIG. 3B illustrates a side view of the sealed state of the self-applicable condom using the preferred embodiment of the present disclosure. The apparatus is viewed in an upright vertical orientation. In the preferred embodiment's sealed state (302), the contents of the self-applicable condom are held within the inner walls of the condom holder (104). The condom body (102) is disposed inwards in a rolled-up fashion, and the condom wrap (106) is disposed in a folded manner. The term folded or compressed may be used interchangeably for this purpose. The condom body (102), condom wrap (106), and the amount of opening space (116) are disposed within the condom holder (104) along a direction (316) such that their size is reduced to the length of the condom holder's (104) inner walls. The condom base ring (112) is attached to the base opening of the condom holder (104) in the same way as in FIG. 3A. The distal end (108) of the condom is also compressed to a smaller size to fit inside the condom holder's (104) inner walls. The condom tip (110) and tip clip (114) are rotated to the side to fit inside the condom holder's (104) inner walls. In doing so, a portion of the distal end (108) is folded to accommodate this rotation. The base seal cover (118) with its attached base latch tab (120) covers the base opening of the condom holder (104). An additional seal cover with an attached latch tab, hereinafter called front seal cover (318) and front latch tab (320), respectively, is attached to the front opening of the condom holder (104). This smaller front seal cover (318) with its front latch tab (320) covers the front of the condom containing the condom tip (110) and tip clip (114). The front seal cover (318) with the front latch tab (320) moves in an outward direction (306) as it is removed from the condom holder (104).

In some way, the packaging design presented with the preferred embodiment's sealed state (302) allows the self-applicable condom apparatus to maintain its small, compact size. The apparatus can fit inside a pant pocket or wallet; the outer walls of the condom holder (104) protect the condom (102, 108, 110, 112) from breaking. Also, the final packaged product can be stacked nicely to save batch packaging space during distribution. In another embodiment, an external container covers the entire apparatus for distribution, sale, and storage. In one sense, this further protects the apparatus during manufacturing and distribution. However, when it comes to the user's experience, this may take up extra time in unpacking, which may distract the user during sexual intercourse.

The packaging of the hinged tip clip (114) shows another aspect of portability for the condom holder (104). Even when the condom (102, 108, 110, 112) is compressed/folded, the hinged tip clip (114) protrudes past the front opening of the condom holder (104). To mitigate this, both the hinged tip clip (114) and the condom tip (110) are rotated to the side on a 90° angle along a horizontal axis; this axis is perpendicular to the condom holder (104) and its top and bottom openings. So, in viewing FIG. 3B in an upright orientation, the condom tip (110) and tip clip (114) can rotate to its left or right along this horizontal axis. When the front seal cover (318) is removed (306), the hinged tip clip (114) and condom tip (110) can be rotated from the sealed state (302) to point outwards. This movement of the hinged tip clip (114) and condom tip (110) can be an automatic springing motion, or it can be done manually.

In another embodiment, the hinged tip clip (114) comprises an additional portion that is disposed sideways with respect to the direction (316) for fitting within the condom holder (104) rather than the entire clip (114). In another sense, the hinged tip clip (114) will have an extra joint or hinge to allow this rotation, resulting in the additional portion. This way, the condom tip (110) does not have to bend when being packed inside the condom holder (102), which lessens the stretching of the condom (102, 108, 110, 112) inside the condom holder (104) and reduces the risk of the condom (102, 108, 110, 112) breaking even further.

Furthermore, this can address the limitation of the hinged tip clip (114) being placed in a horizontal orientation (holding the left and right of the condom tip (110)) in an earlier mentioned alternative embodiment. Whereas a vertically-oriented tip clip (114) in the present disclosure can neatly rotate to fit by folding the distal end of the condom (108) and condom wrap (106), a horizontally-oriented tip (114) may not fit when folded in the same manner. Worse, the handle (204) and attached (202) portions of the hinged tip clip (114) may press on the condom body (102), which may cause the condom (102, 108, 110, 112) to break if pressed too forcefully in such a manner. Making a rotatable portion in the manner previously mentioned would allow the hinged tip clip (114) to fit into the apparatus regardless of its orientation.

In a non-limiting embodiment, the size difference between the front and base openings is a good indicator of which side to apply the condom on: the larger base opening is where the penis is inserted, and the smaller front opening is where the hinged tip clip (114) is located. The base and front seal covers (118, 318) illustrate the difference in their sizes. Further indications can be made in other embodiments to make the direction of application even clearer. This could include, but are not limited to: arrow indicators on the condom holder (104); visual markings on the seal covers (118, 318); different shaped latched tabs (120, 320) attached to their respective seal covers (118, 318). In other embodiments, in addition to the difference in dimensions of the front and base openings, the base seal cover (118), front seal cover (318), and/or their respective tabs (120, 320) may have different colors, patterns, or visual indicators for easy identification. In a non-limiting embodiment, the front opening (318) and/or front tab (320) may have a red color, whereas the base opening (118) and base tab (120) may have a green color.

The front and back seal covers (118, 318) can be made of a flexible material such as, but not limited to, foil, plastic, or film, which makes an airtight seal around the openings of the condom holder (104) apparatus. The adhesive used for the seal covers (118, 318) can be any suitable type (e.g., adhesive), but should preferably be a type that allows the user to easily peel the seal covers (118, 318). Additionally, the adhesive should not be detrimental to the physical or chemical integrity of the condom (102, 108, 110, 112) and condom holder (104). In another embodiment, the seal covers (118, 318) can be made of hard plastic that snaps onto the condom holder (104) openings, which provides further protection to the condom (102, 108, 110, 112) within.

The condom holder (104) is illustrated with a fixed thickness in order to show how the whole apparatus can be contained. In another embodiment, the condom holder (104) can be thinner to better maintain a small, compact size for the apparatus. However, extra packaging may be required to protect the apparatus and the attached condom (102, 108, 110, 112).

FIG. 3C illustrates a side view of the self-applicable condom in a sealed state using the alternative embodiment of the present disclosure. The apparatus is still viewed in an upright vertical orientation, like in FIG. 3B. In the alternative embodiment's sealed state (304), the contents are held within the inner walls of the condom holder (104), much in the same way as FIG. 3B. The condom body (102) is compressed inwards in a rolled-up fashion, and the condom wrap (106) is also compressed; the condom body (102), condom wrap (106), and the amount of opening space (116) are reduced in size to the length of the condom holder's (104) inner walls. The condom base ring (112) is attached to the base opening of the condom holder (104) in the same way, as shown in FIG. 3A. The distal end (108) of the condom is also compressed to a smaller size to fit inside the condom holder's (104) inner walls. The left and right sides of the condom tip (110) are now secured inside the unhinged pinching tip clip (212) via the unhinged clip opening (214). The unhinged clip opening (214) compresses the condom tip (110) laterally, fitting the condom tip (110) within the space of the unhinged clip opening (214); the condom tip's (110) width along the horizontal transverse plane has decreased while its height dimensions along a vertical sagittal plane have increased. In non-limiting embodiments, the unhinged clip (212) is attached to the condom holder (104) via a snap-on mechanism. The face of the unhinged pinching tip clip (212) at the rear base containing the unhinged clip opening (214) is facing the front opening of the condom holder (104) when attached. The base seal cover (118) with the base latch tab (120) covers the base opening of the condom holder (104).

Figure 4A:
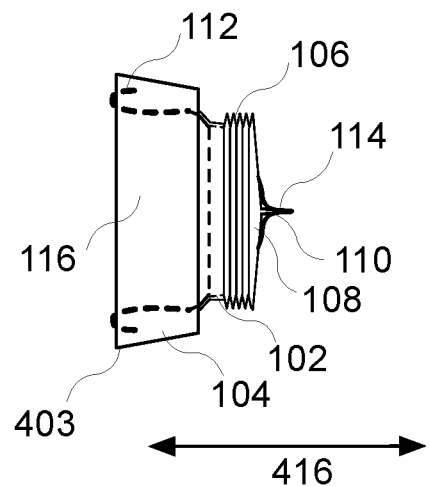
FIG. 4A is the side view of the unsealed state of the self-applicable condom.
Figure 4B:
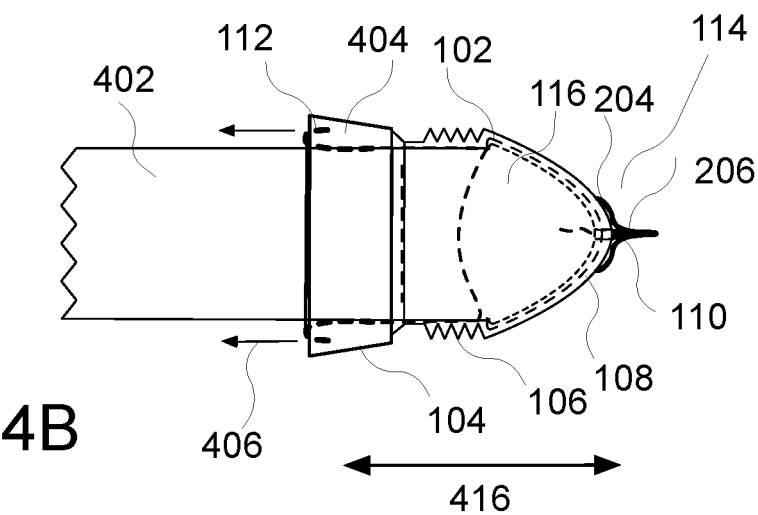
FIGS. 4B-4C are the side views of the application process for the self-applicable condom using the preferred embodiment of the present disclosure.
Figure 4C:
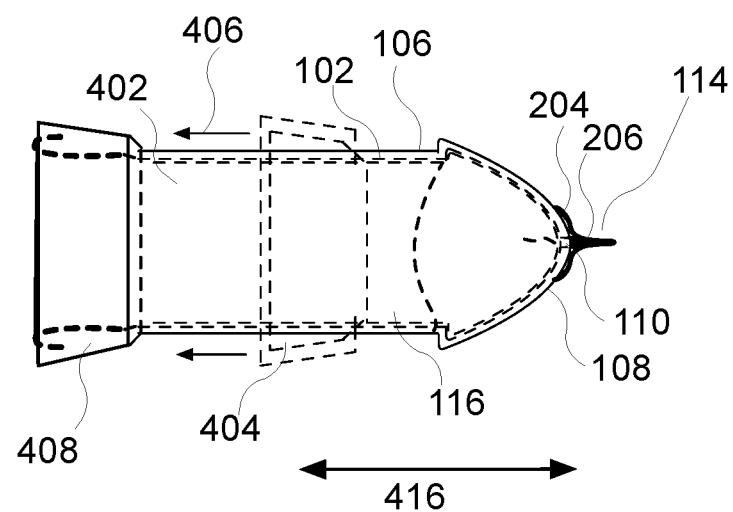

As noted above, FIG. 4A is a side view of the unsealed state of the self-applicable condom, and FIGS. 4B-4C are the side views of the application process for the self-applicable condom using the preferred embodiment of the present disclosure. The apparatus is viewed in an upright vertical orientation. FIG. 4A illustrates the unsealed state of the self-applicable condom using the preferred embodiment of the present disclosure. In the preferred embodiment's unsealed state (403), the condom body (102), condom wrap (106), the distal end (108), the condom tip (110), and the hinged tip clip (114) protrude out the front opening of the condom holder (104) ring. This protrusion expands the opening space (116) within the condom body (102) for inserting the penis. The condom base ring (112) is still held in place at the base opening of the condom holder (104). In addition, the tip (110) and tip clip (114) rotate outwards from its packaged state to face straight forwards (i.e., along the direction (416)).

FIG. 4B illustrates the initial stage of the application process for the self-applicable condom using the preferred embodiment of the present disclosure. Here, an erect penis (402) is inserted through the base opening of the condom holder (104). As the erect penis (402) is inserted, the condom body (102), condom wrap (106), the condom's distal end (108), condom tip (110), and tip clip (114) protrude out of the front opening of the condom holder (104). Most notably, the distal end (108) of the condom (102, 108, 110, 112) is applied onto the glans at the front of the erect penis (402). The condom body (102) partially covers the penis (402) during the initial application. The condom holder (104) is initially disposed at a starting position (404) and is moved in a direction (406) along the penis (402) towards the base of the penis (402) or root; this will be shown in FIG. 4C. At the same time, the condom wrap (106) also expands along the penis (402) in line with the condom application. Lubricant is applied to the condom (102, 108, 110, 112) as the condom wrap (106) expands along the penis (402). In some embodiments, the condom (102, 108, 110, 112) is pre-lubricated. The clamping portion (206) of the hinged tip clip (114) is already pinching the condom tip (110) at this time. The handle portion (204) of the hinged tip clip (114) is shaped along the condom's distal end (108) and the glans of the penis (402).

Since the hinged tip clip (114) is already pinching the condom tip (110), the user does not need to take time to do so, which quickens and eases the process of putting a condom (102, 108, 110, 112) on. In other words, the tip clip (114) reduces the risk of improper application or breaking the condom (102, 108, 110, 112); thus, making the use of the condom (102, 108, 110, 112) safer and user friendly.

FIG. 4C illustrates the self-applicable condom moving along the penis to apply the condom using the preferred embodiment of the present disclosure. As stated in the description of FIG. 4B, the condom holder (104) starts at the initial position (404) once the glans is covered by the distal end (108) of the condom (102, 108, 110, 112). As the condom holder (104) moves to the penis (402) root, the folds of the condom wrap (106) in FIG. 4B expand along the penis (402) in a direction (406) towards the penis (402) root. The condom (102, 108, 110, 112) is then fully applied on the penis (402). When the condom base ring (112) covers the penis (402) root, the condom holder (104) then rests at the final position (408) prior to its ejection. As the condom (102, 108, 110, 112) unrolls along the penis (402), the condom base ring (112) is held in place until the condom (102, 108, 110, 112) is fully applied. At this point, the condom base ring (112) detaches from the base opening of the condom holder (104). The tip (110) and tip clip (114) shown in FIG. 4C is still secured in place during the entire application process.

The user's one hand mainly touches the condom holder (104) rather than the condom body (102) itself. The condom holder (104) itself helps reduce the need to manually handle the condom (102, 108, 110, 112). In another embodiment, regularly-spaced finger-tip indentations can be made around the condom holder (104) ring: preferably one indentation per finger (not shown). This makes the condom holder (104) easier to hold and improves condom application by making the task quicker and easier.

Due to the hinged tip clip (114) pinching the condom tip (110), there is nearly no opening space (116) present between the condom body (102) and the penis (402). As the condom (102, 108, 110, 112) is being applied via the condom holder (104), the hinged tip clip (114) keeps air out of the condom body (102) during application. This improves the condom application experience since it reduces the chances of condom breakage and misuse in three ways: (1) no air bubbles are formed during condom application; (2) the reservoir is created at the condom tip (110) to catch semen; and 3) the semen will not escape to the base of the condom (102, 108, 110, 112).

The hinged tip clip (114) in both FIG. 4B and FIG. 4C is held in place while the condom holder (104) slides along the penis (402)—this is considered one variant of the preferred embodiment and will be explained further in FIGS. 5A-5B. In another variant of the preferred embodiment, the penis (402) or, specifically, the glans of the penis (402) exerts a light pushing force onto the hinged tip clip (114). Because the hinged tip clip (114) is lightweight, this gentle push is enough to open up the handle portion (204) and dislodge the entire clip (114). The condom tip (110) is then released. It is preferred that the hinged tip clip (114) stays on for the entire application when the condom (102, 108, 110, 112) is applied onto the penis (402) since air is less likely to enter throughout the rest of the condom application process.

In the alternative embodiment of the present disclosure involving the unhinged pinching tip clip, the apparatus applies the condom onto the penis (402) in a similar manner as the preferred embodiment. However, the unhinged pinching tip clip is much heavier than the preferred embodiment's tip clip (114); the gentle pushing force exerted by the glans at the beginning of the condom application may not be enough to eject the unhinged pinching tip clip. In this scenario, an additional pushing force may be required to disconnect the condom holder (104) from the unhinged pinching tip clip. When putting on the condom (102, 108, 110, 112) with the apparatus, two non-limiting occurrences may happen with the unhinged pinching tip clip: (1) the weight of the unhinged pinching tip clip causes the part to fall off automatically; (2) the unhinged pinching tip clip slightly falls off and hangs mid-air along with the distal end (108) and the condom tip (110). The condom wrap (106) covering these condom areas (108, 110) also hangs mid-air. As the condom holder (104) slides along the penis (402) shaft to the penis root, the condom holder (104) drags the condom body (102) back towards the root. The condom wrap (106), condom's distal end (108), condom tip (110), and unhinged pinching tip clip are brought back to the same level as the erect penis (402). An airtight seal can still be formed during condom application due to the condom tip's (110) attachment to the cap.

The self-applicable condom apparatus should be applied with enough tightness to ensure that no air is trapped within the condom's opening space (116). In other words, the condom body (102) should embrace/wrap around the penis (402) in such a manner that there is no air between the penis (402) and the condom (102, 108, 110, 112). Additionally, it should provide enough stimulation to keep the penis (402) erect. However, the apparatus is not ideal if it is too tight to the point where it causes users pain. This could be because the penis (402) may be too large to fit through the inner diameter of the condom holder (104). In other embodiments, the condom holder (104) can have varying diameters for different girth sizes while also accommodating different condoms (102, 108, 110, 112) with varying sizes. In yet another embodiment, the condom holder (104) is adjustable to fit different girth sizes.

In yet another embodiment, cushioning can be implemented at the inner diameter of the condom holder (104) to soften the feeling of the condom holder (104) sliding along the penis (402) while still providing enough stimulation to keep the penis (402) erect.

Figure 5A:
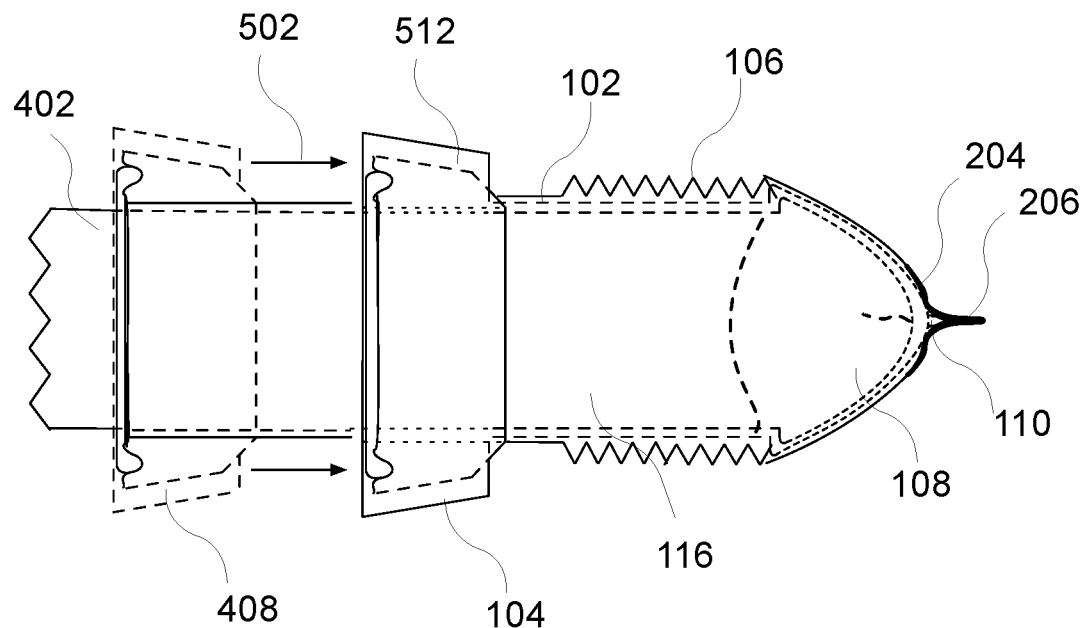
FIGS. 5A-5B are the side views of the ejection process for the self-applicable condom using the preferred embodiment of the present disclosure.
Figure 5B:
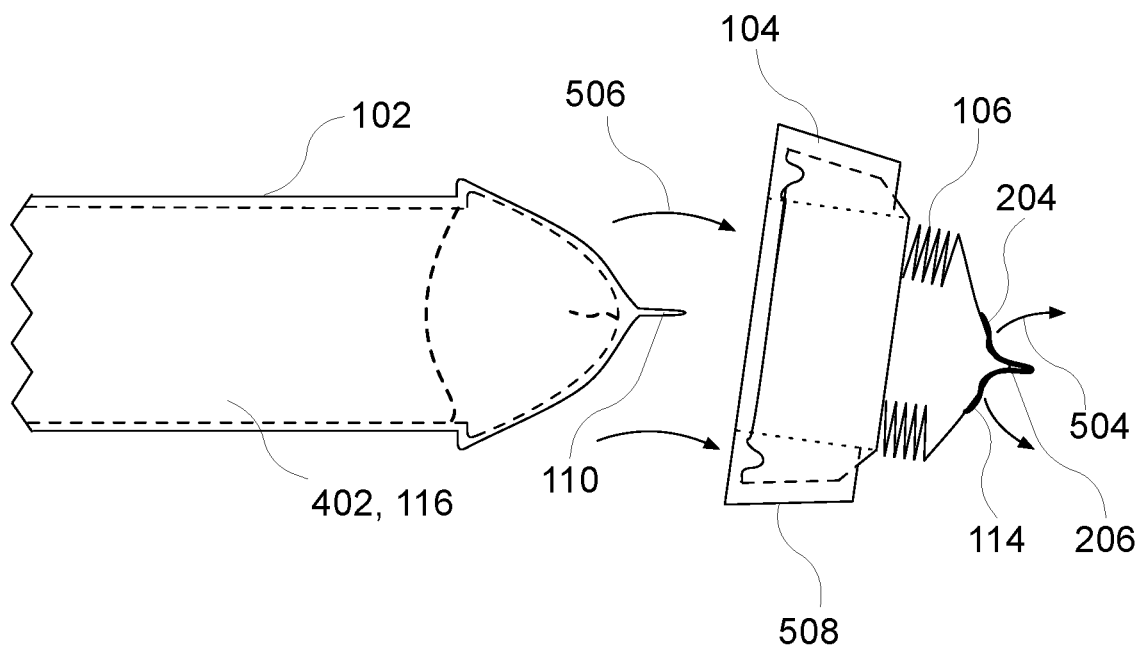

FIGS. 5A-5B illustrate a side view of the ejection process for the self-applicable condom using the preferred embodiment of the present disclosure. FIG. 5A illustrates the beginning stage of the apparatus' ejection. The condom holder (104) completely applies the condom (102, 108, 110, 112) onto the penis (402) and is held at the position (408) near the penis (402) root, as shown in FIG. 4C. From that position (408), the condom holder (104) moves in an outwards direction (502) along the penis (402) towards the penis (402) tip. As it moves to a partially ejected position (512), the condom wrap (106) compresses to a smaller size. This partially ejected position (512) is similar to what is seen in FIG. 4B. As the condom (102, 108, 110, 112) is completely applied onto the penis (402), the condom (102, 108, 110, 112) remains on with nearly no opening space (116) between the penis (402) and condom body (102). At this point, the handle portion (204) and the clamping portion (206) of the hinged tip clip (114) still hold the condom tip (110) in place.

When the condom (102, 108, 110, 112) is fully applied onto the penis (402), there is a slight opening due to the difference in diameter between the applied condom (102, 108, 110, 112) and the inner diameter of the condom holder (104). Because of this, the condom holder (104) can easily slide outwards without affecting the condom (102, 108, 110, 112) itself. This is further aided with lubrication applied to the condom (102, 108, 110, 112). As a result, the condom (102, 108, 110, 112) is less likely to break due to friction or forceful removal of the apparatus.

FIG. 5B illustrates the ejection of the self-applicable condom apparatus. At this point, the condom (102, 108, 110, 112) is fully applied onto the penis (402) with nearly no air or space left in the opening space (116). As the condom holder (104) continues to move outwards to the front tip, the condom wrap (106) is compressed even further. The condom holder (104) also comes in contact with the hinged tip clip (114), which causes the handle portion (204) and clamping portion (206) to open up and expand in an outwards direction (504), releasing the condom tip (110) as a reservoir. The condom holder (104) ejects in a direction (506) away from the penis (402) to a displaced position (508), along with the rest of the apparatus (i.e., condom wrap (106) and tip clip (114)). The apparatus is then disposed of entirely as one waste product.

The apparatus' ejection demonstrates an improvement in the condom application experience in many ways. It is done quickly and effortlessly with no additional handling required. It can also be compacted into a small size to be neatly disposed of. In an alternative embodiment, the apparatus components are ejected separately; however, this may waste additional time for the user during sexual intimacy.

The tip clip's (114) ejection due to contact with the condom holder (104) is one variant of the preferred embodiment. As mentioned earlier, another variant of the preferred embodiment involves the hinged tip clip (114) ejecting separately from the entire apparatus. Because of the tip clip's (114) light mass, the gentle push exerted by the glans of the penis (402) is enough to dislodge the tip clip (114). As the condom (102, 108, 110, 112) has already been applied partway along the penis (402), the reservoir created at the condom tip (110) is still sufficient for ensuring an airtight application of the condom (102, 108, 110, 112) onto the penis (402).

In the alternative embodiment involving the unhinged pinching tip clip, the unhinged clip can be detached as a separate component or as part of the entire apparatus. As noted earlier, the unhinged pinching tip clip falls off from the condom tip (110) on its own once detached from the condom holder (104). The unhinged clip can also fall off when it comes in contact with the ejecting condom holder (104) after the condom is completely put on the penis (402). This happens when the distal end (108), the condom tip (110), and unhinged pinching tip clip are dragged back along the erect penis (402) during condom application. Regardless of how the unhinged clip falls off, no extra effort or time is needed from the user to handle the unhinged pinching tip clip during condom application.

In another embodiment, the condom holder (104) can be made with detachable hinge points to allow for lateral removal from the side of the penis (402). The condom holder (104) in the present disclosure should not affect the applied condom (102, 108, 110, 112) as it slides outwards for ejection. However, if the apparatus is too tight, the holder (104) may come in contact with the condom (102, 108, 110, 112) once again, which may cause areas of the condom (102, 108, 110, 112) to loosen and create gaps or air bubbles within the opening space (116). This may ruin the airtight seal created during condom application. Worse, a tightly-fitted condom holder (104) that slides outwards may also tear the condom (102, 108, 110, 112). By giving the condom holder (104) detachable hinge points to open up and move laterally, the condom holder (104) does not touch the condom (102, 108, 110, 112) after its application onto the penis (402). As a result, the condom (102, 108, 110, 112) is more likely to retain its airtight seal. However, this also means that the condom wrap (106) and the hinged tip clip (114) have to be disposed of separately.

The invention claimed is:

1. An apparatus serving as applicator and container of a male condom with a base, body, and tip for a penis with a root, shaft, and glans, comprising:
   a generally tubular holder with a top and bottom opening;
      wherein the base of the condom is initially installed and held at the bottom opening and the tip of the condom is contained between the top and bottom openings;
      wherein the condom body is rolled into an annular configuration;
   a clip for compressing the condom tip;
      wherein the clip keeps air out of the condom tip;
   a compressed condom wrap that initially covers the condom body from the bottom opening to the top opening and extends from the top opening after the penis glans enters the holder and container from the condom base at the bottom opening; wherein the holder unrolls the condom by moving towards the penis's root until the condom is entirely wrapped around the penis shaft; wherein the holder detaches the wrap and itself from the condom body by moving away from the penis' root; wherein the clip is also released from the condom tip with the wrap.

2. The apparatus of claim 1, wherein the condom wrap is generally shaped like the condom completely covers the condom from the top opening side and is integrated with the holder at the bottom opening side; wherein the clip compresses the condom tip through the wrap from the outside; wherein the clip may be attached to the condom wrap.

3. The apparatus of claim 1, wherein the clip is a resilient hinged clip comprising a clamp portion that compresses the condom tip tightly and a handle or attached portion extending from the clamp portion on each side.

4. The apparatus of claim 1, wherein the clip is a resilient unhinged clip with a generally flat surface and a slit between a first and second edge to compress the condom tip tightly;

wherein the first and second edges are along the slit's length; wherein the slit opens wider when the two edges are pressed and is otherwise closed.

5. The apparatus of claim 2, wherein the wrap, holder, or clip touches the penis and provides stimulus to keep the penis erect during the condom application; wherein lubricant is applied between the condom and condom wrap.

6. The apparatus of claim 1, wherein the clip holds the condom tip using a snapping mechanism.

7. The apparatus of claim 6, wherein the snapping mechanism is a snap-on or snap-fit mechanism.

8. The apparatus of claim 6, wherein the holder contains multiple parts and one of the parts attaches to another through the same snapping mechanism.

9. The apparatus of claim 1, wherein the base of the condom is detachably locked in a mechanism at the bottom opening of the holder.

10. The apparatus of claim 9, wherein the locking mechanism is a ring groove on the holder.

11. The apparatus of claim 1, further comprising a bottom seal cover that covers the bottom opening of the holder; a top seal cover that covers the top opening; wherein the top or bottom seal cover may have a latch tab that can be grasped by the user to peel the cover off the holder.

12. The apparatus of claim 11, wherein the top and bottom seal covers and holder form a package for the condom; wherein the condom is stored in the hollow space defined between the top and bottom openings of the holder.

13. The apparatus of claim 12, wherein the hinged tip clip is folded sideways for a more compact packaging.

14. The apparatus of claim 1, wherein the top and bottom openings of the holder have different dimensions; wherein the dimension of the top opening may be larger than that of the bottom opening.

* * * * *